(12) United States Patent
Steward et al.

(10) Patent No.: US 6,214,327 B1
(45) Date of Patent: *Apr. 10, 2001

(54) ANTIBACTERIAL COMPOSITION

(75) Inventors: Howard N. Steward, Milwaukie, OR (US); Lee L. Paler, Oceanside; John A. Garruto, Cardiff, both of CA (US)

(73) Assignee: Bio-Safe Enterprises, Inc., Milwaukee, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/351,378

(22) Filed: Jul. 12, 1999

Related U.S. Application Data

(63) Continuation of application No. 09/016,466, filed on Jan. 30, 1998, now Pat. No. 5,922,313, which is a continuation of application No. 08/671,148, filed on Jun. 24, 1996, now abandoned.

(51) Int. Cl.[7] .............. A61K 7/06; A61K 9/36; A61K 31/155; A61K 31/045
(52) U.S. Cl. ............ 424/70.15; 424/480; 514/635; 514/728; 514/731
(58) Field of Search ................. 424/70.15, 480; 514/635, 728, 731

(56) References Cited

U.S. PATENT DOCUMENTS

| | | | |
|---|---|---|---|
| 2,900,305 | 8/1959 | Siggia | 524/548 |
| 3,950,554 | 4/1976 | Prince | 514/390 |
| 3,993,777 | 11/1976 | Caughman et al. | 514/642 |
| 4,067,967 | 1/1978 | Prince | 424/672 |
| 4,199,564 | 4/1980 | Silver et al. | 514/358 |
| 4,301,145 | 11/1981 | Cestari | 424/78.07 |
| 4,311,709 | 1/1982 | Dybas et al. | 514/649 |
| 4,406,884 | 9/1983 | Fawzi et al. | 514/557 |
| 4,512,987 | 4/1985 | Schindlery | 514/171 |
| 4,584,192 | 4/1986 | Dell et al. | 424/78.07 |
| 4,671,957 | 6/1987 | Holtshousen | 424/78.06 |
| 4,915,940 | 4/1990 | Saitoh et al. | 514/481 |
| 4,919,837 | 4/1990 | Gluck | 510/386 |
| 4,942,029 | 7/1990 | Scheps | 424/78.07 |
| 5,173,291 | 12/1992 | Brink et al. | 180/408 |
| 5,232,691 | 8/1993 | Lemole | 424/78.2 |
| 5,254,334 | 10/1993 | Ramirez et al. | 424/70.24 |
| 5,288,493 | 2/1994 | Martino et al. | 424/401 |
| 5,336,305 | 8/1994 | Staats | 106/18.32 |
| 5,409,697 | 4/1995 | Gluck | 424/78.25 |
| 5,409,706 | 4/1995 | Ramirez et al. | 424/401 |
| 5,417,968 | 5/1995 | Staats | 424/78.07 |
| 5,482,720 | 1/1996 | Murphy et al. | 424/489 |
| 5,503,838 | 4/1996 | Schmidt et al. | 424/407 |
| 5,531,984 | 7/1996 | Staats | 424/78.07 |
| 5,922,313 * | 7/1999 | Steward et al. | 424/70.15 |

FOREIGN PATENT DOCUMENTS

| 86/05391 | 9/1986 | (WO) . |
| 95/25544 | 9/1995 | (WO) . |

OTHER PUBLICATIONS

Chemical abstract (107:64896) Gluck, WO 8605391, 1986.

* cited by examiner

*Primary Examiner*—Kevin E. Weddington
(74) *Attorney, Agent, or Firm*—Kolisch Hartwell Dickinson McCormack & Heuser

(57) ABSTRACT

Lotion compositions for applying topically to skin include a barrier-forming polymer mixture and an anti-microbial agent. The polymer dries on skin to form a barrier which prevents pathogens, solvents and petrochemicals from penetrating into the skin. The barrier is resistant to being washed off for at least several hours, during which time the antibacterial agent effectively kills a broad spectrum of bacteria within seconds after contact.

16 Claims, No Drawings

ANTIBACTERIAL COMPOSITION

CROSS-REFERENCE TO RELATED APPLICATION

This application is a continuation of U.S. patent application Ser. No. 09/016,466, filed Jan. 30, 1998, now U.S. Pat. No. 5,922,313, which is a continuation of U.S. patent application Ser. No. 08/671,148, filed Jun. 24, 1996, now abandoned.

FIELD OF THE INVENTION

The invention relates to compositions and methods for protecting skin and preventing carryover of biohazardous substances from one material to another. In particular, the invention involves lotion compositions which are applied on skin to form a protective polymer coating while also being capable of rapidly killing a broad spectrum of microbial pathogens.

BACKGROUND OF THE INVENTION

There are many situations where people need to expose their hands to potentially hazardous materials including microorganisms, chemicals, etc., in connection with their work. A few examples of workers who manually encounter biohazards in their jobs include restaurant workers, food processors in meat and poultry plants, health care professionals such as physicians, nurses, emergency medical technicians, police, prison guards, fire fighters, mechanics, etc. In the food service and processing industries, workers hands frequently contact pathogenic organisms which can be dangerous to the worker or to the recipients of the processed food. In the past several years the public has been especially aware of this problem with respect to the handling of meat and poultry due to severe illness caused by the bacteria *E.coli* and Salmonella.

Workers' hands also come into contact with hazardous chemicals such as commercial solvents and petrochemicals which may damage the worker's skin and/or be absorbed through the skin possibly carrying other hazardous solutes and causing internal toxicity.

In coming up with a strategy for protecting people from manually encountered biohazards in the workplace, it is important to consider the need to protect the worker as well as the need to protect the consumer. For example, the most common approach for protecting a worker's hands from biohazardous organisms or chemicals is to wear gloves. However, even if a glove material is capable of acting as a complete barrier protecting the worker's hands, the gloves do not prevent carryover (cross contamination) of hazardous materials from one material to another. A worker wearing gloves may work with hamburger one minute and make a salad minutes later without changing gloves. This may result in carryover or cross-contamination of a hazardous substance or pathogen from one food to another. Accordingly, even if gloves protect the worker's skin, they do not adequately protect others who may be injured from carryover of hazardous materials in the workplace.

Another problem with gloves is that they reduce the worker's dexterity. This causes some workers not to wear gloves even in situations where there are dangerous chemicals or pathogens in the work environment. For example, machinists and mechanics frequently have to manipulate devices in small spaces or compartments where solvents and petrochemicals are present. The worker may not wear gloves in these situations because to do so would compromise the worker's agility or dexterity, thus slowing down or preventing the worker from carrying out his work. Gloves also significantly limit or prevent the worker from using his sense of touch which may be essential to the activity.

Accordingly, an important object of the present invention is to provide an alternative to wearing gloves which protects the users hands from biohazardous materials while also preventing cross contamination.

A further object of the invention is to provide a lotion for use on hands which is capable of broad spectrum bactericidal and antiviral activity within seconds of contact. The lotion should maintain its anti-microbial efficacy for at least several hours after application to the skin.

Another important object of the invention is to provide a polymer-based barrier on the skin which resists being washed-off and which prevents absorption through the skin of hazardous chemicals and commercial solvents.

Another goal of the invention is for the lotion's antibacterial and barrier functions to be relatively insensitive to the pH of the hazardous material.

Still another object is for the lotion to be nontoxic to humans.

The lotion should have a useful shelf-life of at least about two years. During that time the solution/emulsion should remain homogenous without any precipitation or separation of phases. The lotion's anti-microbial efficacy must also be maintained during the shelf-life period.

SUMMARY OF THE INVENTION

The present invention provides a lotion for application to skin for the purpose of protecting the skin from biohazardous materials such as solvents and petrochemicals which may damage the skin and/or be absorbed into the skin along with potentially toxic solutes, and for the purpose of preventing cross contamination of potentially hazardous pathogens such as bacteria and viruses from one material to another. One formula of the present invention includes a mire of polyvinylpyrrolidone (PVP) and hydroxyethylcellulose (HEC) in an aqueous solution, and an antibacterial agent dispersed in the solution. In another formula of the invention, the PVP and HEC polymer mixture is replaced by an aqueous carbomer solution. After application to the skin, the polymer material dries into a barrier film which resists being washed off and which prevents a variety of different chemicals and pathogens from contacting or penetrating the skin. The antibacterial agent kills bacteria upon contact or shortly thereafter. Different antibacterial agents are used such as 2,4,4'-trichloro-2'hydroxydiphenylether ("triclosan") or chlorhexidine gluconate. The lotion may also include other materials such as antiviral agents, emulsifying agents, emulsion stabilizers, emollients, plasticizers, preservatives, aloe vera, glycerine and vitamin E.

The polymeric/antibacterial formulas of the present invention are unique and advantageous in their ability to provide a penetrant barrier which resists being washed off while providing broad spectrum anti-microbial efficacy for at least four hours after the lotion is applied to the skin. During that time period, bacteria which comes into contact with the antibacterial barrier is killed within seconds after contact.

Lotions of the present invention are typically produced by first dispersing and dissolving the polymers in water. The solution is then heated to approximately 75–80° C. In a second solution the emulsion, emollient and plasticizer components are mixed and heated to about 75–80° C. The second solution is then added to the first solution and mixed while cooling to about 40° C. A third solution including the antibacterial agent is then mixed into the batch. The solution is mixed while cooling to 35° C. and then the preservative is added. Finally, if necessary, the pH is adjusted to about 6.5–7.0.

DESCRIPTION OF THE INVENTION

The invention provides a number of lotion formulas, each of which, fundamentaly, includes a polymeric film-forming component and an antibacterial agent dispersed in the polymer material. The polymeric component must be selected and formulated so that after application on skin, it dries into a coating which is not easily washed or rubbed off and which serves as a barrier to prevent penetration of hazardous solvents and/or petrochemicals into the skin. The barrier is effective for at least several hours after application. We have discovered at least two different types of polymers which can be used for this purpose. Examples of these polymer formulas are detailed below. Three of the examples described include a mixture of polyvinylpyrrolidone (PVP) and hydroxyethylcellulose (HEC). The PVP preferably has a molecular weight in the range of about 20,000–40,000 daltons and is provided in the solution at a concentration of between approximately 0.10 to 2.00-percent (w/w). The HEC is provided in the solution at approximately 0.10 to 2.00-percent (wlw). In another formula, instead of using PVP and HEC, Carbopol™ 980 (an acrylic polymer) is used at a concentration of between approximately 0.05 to 2.00-percent (w/w). There are many different molecular weights available for these polymers, i.e., 12,000 to 2,800,000. The molecular weights and concentrations of these materials are carefully selected, balanced and stabilized because too much will cause the barrier to disrupt and flake or roll off the skin while too little will provide an inadequate barrier.

Examples of four formulas of the present invention are given below, along with procedures for manufacturing the lotions. The percent figures are in terms of weight/weight. Preferred suppliers for the materials are also set forth. The first three formulas include PVP K-30 and HEC (Natrosol™ 250 HHR) as the film forming polymers. In the fourth formula, Carbopol™ 980 is used instead.

It turned out to be quite difficult to find a combination of polymers that can fill each of the objectives of: (a) remaining homogeneous, while exhibiting a smooth luxurious lotion quality, without causing the antibacterial agent to precipitate or come out of solution, and (b) when applied to the skin, forming a continuous long-lasting, wash-off resistant barrier film that allows the anti-bacterial agent to remain effective over an extended period of time. We discovered that the combination of PVP with HEC satisfied these objectives far better than either ingredient without the other, or any other polymer combination we tried.

Another important component of the composition is an antibacterial agent. The agent must be dispersable and stable at an effective concentration in solution with the polymer mixture and any other necessary dispersing or emulsifying agents, etc. For example, one antibacterial agent which is used in the present invention is 2,4,4'-trichloro-2'-hydroxydiphenylether ("triclosan") at a concentration of between about 0.10 to 2.00-percent (w/w). Another antibacterial agent used in the present invention is chlorhexidine gluconate at a concentration of between about 0.10 to 3.00-percent (w/w).

Another important ingredient of the present invention is an antiviral agent. For example, Carsonan™ N-9 at a concentration of about 0.50-percent (w/w) may be included in the lotion. Carsonan™ N-9 is available from Lonza and is generically known as nonylphenol thoxylate. Nonylphenol thoxylate has been shown to be effective in killing hepatitis B and HIV viruses.

An emulsion stabilzer such as Crodocal™ C-95 provides skin emolliency. An emulsifying agent such as Lipomulse 165 is included in the formula to provide skin conditioning. Lexol™ IPM, a myristic acid ester, is used as an emollient and plasticizer for the barrier film. A preservative such as Germaben™ II-E is also used.

In some instances materials are referred to by the trade names of preferred suppliers. Information about preferred materials are provided below.

PVP K-30 is purchased from ISP.

Natrosol® 250 HHR, hydroxyethylcellulose from Hercules Inc., is a non-ionic water-soluble polymer which is initially provided as a free-granular powder.

Crodacol™ C-95 is cetyl alcohol available from Croda Inc.

Aloe vera powder 200XXX is purchased from Tri-K in the form of a fine powder.

Lexol IPM is obtained from Inolex Chemical Company. It is isopropyl myristate, an ester of isopropyl alcohol and myristic acid.

Vitamin E is purchased from Roche Vitamins and Fine Chemicals.

Chlorhexidine gluconate is obtained from Xtrium in a stock concentration of about 20-percent (w/v). It is also known as 1,1'-hexamethylenebis[5-(4-chlorophenyl) biguanide]digluconate.

Germaben® II-E is a liquid preservative available from Sutton Laboratories. It is a clear viscous liquid including 20-percent diazolidinyl urea, 10percent methylparaben, 10percent propylparaben and 60-percent propylene glycol.

Versene™ XL100 is obtained from Dow Chemical Company. As provided, it is 38-percent tetrasodium salt of ethylene-diaminetetra acetic acid, 61-percent water and 1-percent sodium hydroxide.

Irgasan DP300 is a broad spectrum anti-microbial agent available from Ciba-Geigy Corporation. It is also known as 2,4,4'-trichloro-2'-hydroxydiphenyl or 5-chloro-2-2,4-dichlorophenoxy)phenol or "triclosan."

Carsonon N-9 is nonylphenol thoxylate available from Lonza.

Carbopol® 980 is an acrylic polymer also known as carbomer or carboxy polyethylene available from B.F. Goodrich.

D.C. 200 fluid from Dow Corning is a clear, waterwhite dimethyl polysiloxane fluid.

Lipomulse™ 165 is available from Lipo Chemicals, Inc. It contains approxmately equal parts of glyceryl stearate and PEG-100 stearate.

EXAMPLE 1

| Ingredient | Percent | Supplier |
| --- | --- | --- |
| Part A | | |
| Deionized Water | 90.77 | — |
| PVP K-30 | 0.25 | ISP |

-continued

| Ingredient | Percent | Supplier |
|---|---|---|
| Natrosol 250 HHR | 0.195 | Aqualon |
| Glycerin USP | 1.25 | Dow |
| Aloe Vera Powder 200XXX | 0.002 | Tri-K |
| Part B | | |
| Crodacol C-95 | 0.20 | Croda |
| Lipomulse 165 | 1.06 | Lipo |
| Lexol IPM | 0.15 | Inolex |
| Part C | | |
| Deionized Water | 4.0 | — |
| Chlorhexidine Gluconate | 2.0 | Xttrium |
| Part D | | |
| Germaben II-E | 0.123 | Sutton |

Manufacturing Procedure—Add water to mixing tank. Disperse PVP-K into water until completely dissolved. Next, disperse the Natrosol with good agitation until completely hydrated and solution is clear and free of foreign matter. Add remaining ingredients in part A and mix batch while heating to 75–80° C. Pre-blend ingredients in part B in separate vessel and heat to 75–80° C. Add part B to part A and mix while cooling to 40° C. Pre-blend part C and add to batch. Continue to mix while cooling to 35° C. Add part D and mix completely. If necessary, adjust pH to 6.5–7.0.

EXAMPLE 2

| Ingredient | Percent | Supplier |
|---|---|---|
| Part A | | |
| Deionized Water | 85.56 | — |
| PVP K-30 | 1.00 | ISP |
| Natrosol 250 HHR | 0.78 | Aqualon |
| Glycerin USP | 2.90 | Dow |
| Aloe Vera Powder 200XXX | 0.01 | Tri-K |
| Part B | | |
| Crodacol C-95 | 0.80 | Croda |
| Lipomulse 165 | 4.25 | Lipo |
| Lexol IPM | 0.60 | Inolex |
| Vitamin E Acetate | 0.10 | Roche |
| Part C | | |
| Deionized Water | 2.00 | — |
| Chlorhexidine Gluconate 20% | 1.00 | Xttrium |
| Part D | | |
| Germaben II-E | 1.00 | Sutton |

Manufacturing Procedure—Add water to mixing tank. Disperse PVP K-30 into water until completely dissolved. Next, disperse the Natrosol with good agitation until completely hydrated and solution is clear and free of foreign matter. Add remaining ingredients in part A and mix batch while heating to 75–80° C. Pre-blend ingredients in part B in separate vessel and heat to 75–80° C. Add part B to part A and mix while cooling to 40° C. Pre-blend part C and add to batch. Continue to mnix while cooling to 35° C. Add part D to mix completely. If necessary, adjust pH to 6.5–7.0.

EXAMPLE 3

| Ingredient | Percent | Supplier |
|---|---|---|
| Part A | | |
| Deionized Water | 86.58 | — |
| Versene XL 100 (to pH = 8.0–9.0) | 0.02 | Dow |
| PVP K-30 | 0.85 | ISP |
| Natrosol 250 HHR | 0.70 | Aqualon |
| Glycerin USP | 2.00 | Dow |
| Part B | | |
| Crodacol C-95 | 1.20 | Croda |
| Lipomulse 165 | 4.25 | Lipo |
| Lexol IPM | 0.50 | Inolex |
| Vitamin E Acetate | 0.10 | Roche |
| Irgasan DP300 | 0.50 | Ciba-Geigy |
| Dow Corning 200 Fluid (350 cps) | 1.70 | Dow Corning |
| Carsonon N-9 | 0.50 | Lonza |
| Part C | | |
| Germaben II-E | 1.00 | Sutton |

Manufacturing Procedure—Add water to mixing tank and adjust pH. Disperse PVP into water with good agitation and mix until completely dissolved. Sift Natrosol into batch and mix until completely clear and free of particles. Add remaining ingredients in part A and mix batch while heating to 75–80° C. Pre-blend ingredients in part B in separate vessel and heat to 75–80° C. Add part B to part A and continue mixing batch while cooling to 40° C. Add part C to batch and mix completely. Continue to mix while cooling to 35° C.

EXAMPLE 4

| Ingredient | Percent | Supplier |
|---|---|---|
| Part A | | |
| Deionized Water | 81.51 | — |
| Carbopol 980 | 0.10 | B. F. Goodrich |
| Glycerin USP | 2.00 | Dow |
| Versene NA2 | 0.05 | Dow |
| Part B | | |
| Lipomulse 165 | 5.00 | Lipo |
| Liponate SPS | 1.00 | Lipo |
| Emersol 132 | 1.50 | Wilchem |
| Carsonon N-9 anti viral | 0.50 | Lonza |
| Lexol IPM | 0.50 | Inolex |
| Dow Corning 200 Fluid (350 cps) | 1.20 | Dow Corning |
| Vitamin E Acetate | 0.10 | Roche |
| Irgasan DP300 | 0.30 | Ciba-Geigy |
| Part C | | |
| Deionized Water | 1.00 | — |
| Triethanolamine 99% | 0.34 | Union Carbide |
| Part D | | |
| Germaben II-E | 1.00 | Sutton |
| Fragrance #081411-393R | 0.30 | Belmay |
| Glydant | 0.30 | Lonza |
| Part E | | |
| Deionized Water | 3.00 | — |
| PVP K-30 | 0.30 | ISP |

Manufacturing Procedure—Add water to mixing tank. Disperse Carbopol into water with good agitation and mix until completely dissolved. Add remaining ingredients in part A and mix batch while heating to 75–80° C. Pre-blend ingredients in part B in separate vessel and heat to 75–80° C. Add part B to part A and continue mixing. Pre-blend part C and add to batch. Continue mixing batch and being cooling to 40° C. Add part D to batch in order shown and mix completely. Pre-blend part E with good agitation. Mix until completely clear and free of particles and add to batch. Continue to mix while cooling to 35° C. If necessary, adjust pH to 6.5–7.0.

EXPERIMENTAL RESULTS

Experiment No. 1

In this experiment, lotion of the formula given in example 3 above was applied to excised skin samples and challenged with pure cultures of E.coli, Salmonella and *Staphylococcus aureus*. Each sample was challenged with liquid broth containing over $10^7$ organisms per millimeter. Microbial challenge was made four hours after the lotion was applied. Impressions of the skin onto blood agar plates were done in as little as five seconds and up to five minutes after bacterial contact on the skin. Control samples were challenged without lotions. Results were based on visual evaluation of the blood agar plates after the impressions had been made by the skin samples and after at least twelve hours of incubation at 37° C. A visual evaluation scale is described below.

Method

Fresh biopsied skin from baby pigs that had recently died from natural causes were prepared for the study by excision of the dermal and epidermal layers. Excised skin was shaved with a straight-edge razor to prepare a smooth epidermal layer. Sections approximately 3 cm×3 cm were kept in saline at 4° C. until used. The samples were washed with soap and water and rinsed in isopropyl alcohol but were not disinfected with anything that may have a residual effect. In each study control skin samples, without lotion applied, were compared to the treated samples. The treated samples were prepared by rubbing a small amount of lotion onto the surface and rubbing it into the skin. Excess lotion was removed with a clean towel and each sample was put in a 30° C. chamber to simulate the temperature of the hands for a period of four hours. The larger section was cut into small squares approximately 0.5 cm to 0.5 cm prior to bacterial challenge.

Each sample was challenged by coating the sample with 2 drops of freshly vortexed (mixed) broth culture of one of the three pathogens containing at least $10^7$ organisms per ml. At the appropriate time interval the skin was pressed five times onto a blood agar plate in different spots to determine the number of viable organisms that could be transferred to the culture plates. The plate was then incubated at 37° C. for at least 12 hours. Growth on the agar plate was scored according to the following scale: 0=no growth, 1=slight growth, 2=moderate growth, 3=heavy growth, 4=very heavy growth.

Contact time of the organisms on the treated and untreated skin was 5 minutes, 2 mninutes, 1 minute, 30 seconds or 0–25 seconds. The 0–25 second sample was made blotting a skin sample and pressing it to the plate as soon as possible. The first impression to the plate was approximately 5 seconds after challenge. The sample was then held for 5 seconds and another impression was made. This was repeated, giving impressions made at 5, 10, 15, 20 and 25 seconds. The 5 second interval impressions were made to show the near-immediate antibacterial effect.

Results

With each organism the score for the control was a 4 (very heavy growth). Significant reduction in organism numbers were seen on the treated samples 4 hours after the lotion was applied and within 5 seconds of contact time. Average scores for each organism type and each time interval are shown in Table 1. There was little difference in effectiveness at the different time intervals. The inhibition essentially the same at a few seconds as it was at 5 minutes.

TABLE 1

Average Bacterial Growth Values (Scored 0–4) of 16 Replicates

| | Time | Control | Bio-Safe Treated |
|---|---|---|---|
| E. coli ($10^8$) | 5 minutes | 4.0 | 1.19 |
| | 2 minutes | 4.0 | 0.94 |
| | 1 minute | 4.0 | 0.87 |
| | 30 seconds | 4.0 | 0.44 |
| | 0–25 seconds | 4.0 | 0.81 |
| Salmonella ($10^7$) | 5 minutes | 4.0 | 0.31 |
| | 2 minutes | 4.0 | 0.69 |
| | 1 minute | 4.0 | 0.25 |
| | 30 seconds | 4.0 | 0.31 |
| | 0–25 seconds | 4.0 | 0.25 |
| S. aureus ($10^7$) | 5 minutes | 4.0 | 0.12 |
| | 2 minutes | 4.0 | 0.19 |
| | 1 minute | 4.0 | 0.19 |
| | 30 seconds | 4.0 | 0.06 |
| | 0–25 seconds | 4.0 | 0.25 |

The average scores for all organisms fell somewhere between no growth and the slight category. In this experiment, Bio-Safe® Antibacterial Lotion was effective in significantly reducing the number of pathogenic organisms on the skin when the microbial challenge was four hours after application of the lotion and even if the contact time with treated skin was only a few seconds. The challenge numbers, i.e., microbial quantity, used in this experiment greatly exceeds typical naturally occurring challenge numbers. The results of this experiment demonstrate that the lotion composition is capable of broad spectrum bactericidal activity within seconds of contact and that the lotion maintains its antibacterial efficacy for up to at least four hours after the lotion is applied to the skin.

Experiment No. 2

This experiment was performed to determine the efficacy of the present invention as a teatdip for cows. Sixteen cows, Holsteins and Jerseys, completed the study. A formula similar to the examples provided above was used in the experiment. The lotion was approximately 90-percent deionized water and included PVP, HEC, stearic acid, vitamin E, aloe vera and triclosan. The condition of each cow's teats was examined and described prior to treatment with the lotion. Teats were then dipped in the lotion on a daily basis for one week. Then, teat condition was examined and described again. The results are reported below in Table 2.

TABLE 2

Skin Condition Before and After One-Week Application of Skin Barrier Treat Dip

| Cow # | Pre-Trial Score | Pre-Trial Comments | Post-Trial Score | Post-Trial Comments |
|---|---|---|---|---|
| Holsteins | | | | |
| 231 | 3 | dry, flowered ends | 1 | smooth, soft |
| 364 | 2 | slight flower LR | 1 | smooth, soft flower |
| 372 | 4 | dry, rough, deep cracks, flowered | 1 | smooth, flowers present but shallow, soft, healing |
| 416 | 3 | damaged sphincter | 1 | smooth, soft |
| 420 | 3 | cracked teat end | 1 | smooth |
| 438 | 2 | smooth, small abrasion RR | 1 | smooth, soft |
| 366 | 3 | all flowered at sphincter | 2 | soft flowering |
| 352 | 3 | damaged teat ends, flowered | 2 | healing flowered ends |
| 407 | 1 | smooth | 1 | smooth, soft |
| 428 | 3 | dry, not chapped | 1 | smooth, soft |
| 392 | 1 | smooth | 1 | smooth, soft |
| 472 | 3 | mild dryness | 1 | smooth, soft |
| Jerseys | | | | |
| 993 | 3 | slight cracking of ends | 1 | smooth |
| 748 | 3 | abrasion, RF | 2 | soft, rough on abrasion |
| 754 | 3 | cracks RR | 2 | soft cracks |
| 991 | 1 | smooth, slight teat end damage | 1 | smooth, soft |

Experimental No. 3

The purpose of this experiment was to assess the skin sensitization potential of lotion according to the formula above given in example 2 when applied topically to the skin of healthy human subjects.

The sensitization potential of the lotion was tested on 55 subjects (11 males and 44 females). Testing was done in accordance with a modified Draize assay employing an 8 millimeter Finn Chamber (occlusive patch).

For the induction phase the product was applied to the scapular back Monday, Wednesday and Friday of each week for three consecutive weeks, with a final patch on Monday of the fourth week, for a total of eight applications. Scoring of the skin sites was made at the end of each 48 hour patch period (72 hours on weekends). The final reading was made on Wednesday of the fourth week. Following a twelve day rest period, each subject received a single 48 hour occlusive challenge patch of the product on a naive skin site on the scapular back. Scoring of the challenge site was made after removal of the patch and again two days later. The following scale was made for scoring:

0=No reaction (negative reading)
1=Erythema throughout the entire patch area
2=Erythema and edema
3=Erythema, edema and vesicles
4=Erythema, edema and bullae Thirty-one subjects patched with the lotion showed a total of 98 1+ reactions and 9 2+ reactions during the induction phase. Two subjects also presented a 1+ reaction at the 48 hour challenge reading. Since 1+ reaction are minimal irritant responses and the 2+ reactions resolved spontaneously, the lotion is judged to be neither a significant irritant nor contact sensitizor.

Experiment No. 4

This experiment was performed to challenge the stability of the lotion formula given above in example 3. The test was performed by BioScreen® Testing Services, Inc. in Torrance, Calif. The test was referred to as U.S.P. Challenge Test with Rechallenge on Day 12. BTS test method M101 from reference U.S.P. 23 was used. The following organisms: *Aspergillus niger, Candida albicans, Escherichia coli, Pseudomonas aeruginosa, Staphylococcus aureus*, were used to challenge the specimen for 28 days at intervals of 7, 14, 21 and 28 days. The product was rechallenged at day 12 with the same organisms.

The results of the experiment are reported below in Table 3.

TABLE 3

| Micro Organism | Initial Inoculum/ml | Colony Forming Units/ml | | | |
|---|---|---|---|---|---|
| | | Day 7 | Day 14 | Day 21 | Day 28 |
| A. niger | $5.2 \times 10^5$ | <10 | <10 | <10 | <10 |
| C. albicans | $5.5 \times 10^5$ | <10 | <10 | <10 | <10 |
| E. coli | $9.3 \times 10^5$ | <10 | <10 | <10 | <10 |
| P. aeruginosa | $7.7 \times 10^5$ | <10 | <10 | <10 | <10 |
| S. aureus | $8.0 \times 10^5$ | <10 | <10 | <10 | <10 |

The preservative is effective if: (a) the concentration of viable bacteria is reduced to not more than 0.1-percent of the initial concentration by day 14, (b) the concentration of viable yeasts and molds remains at or below the initial concentration during the first 14 days, and (c) the concentration of each test microorganism remains at or below these designated levels during the remainder of the 28 day test period.

The data reported in Table 3 shows that preservative was stable and effective for the organisms *Aspergilus niger, Candida albicans, Escherichia coli, Pseudomonas aeruginosa* and *Staphylococcus aureus*. Based on this experiment, we can predict that the lotion of the present invention will have a stable shelf life for at least about 2 years.

Experiment No. 5

This experiment was performed by the test tube dilution method to determine the lowest concentration of test product that will inhibit bacterial growth. This concentration is referred to as the minimum inhibitory concentration (MIC).

The test was done by performing 2-fold cereal dilutions of the test product in broth (1:2 through 1:256) and inoculating the dilutions separately with the test organisms. The concentration of the test product in the last tube that exhibit inhibition (no growth) is reported as the MIC. The test product that shows no inhibition of bacterial growth (growth in all tubes) is reported as "failed."

The lotion was challenged with the following microorganisms: *Escherichia coli* (*EC*), *Enterbacter aerogenes* (*EA*), *Pseudomonas aeruginosa* (*PA*), *Klebsiella pneumoniae* (*KP*), *Micrococcus luteus* (*ML*), *Proteus mirabilis* (*PM*), *Serratia marcescens* (*SM*), *Staphylococcus aureus* (*SA*) and *Streptococcus bovis* (*SB*). The results are reported in Tables 4 and 5 below.

TABLE 4

| Organism | E.A | E.C. | K.P. | M.L. |
|---|---|---|---|---|
| Undilute | − | − | − | − |
| 1:2 | + | + | + | + |
| 1:4 | + | + | + | + |
| 1:8 | + | + | + | + |
| 1:16 | + | + | + | + |
| 1:32 | + | + | + | + |
| 1:64 | + | + | + | + |
| 1:128 | + | + | + | + |
| 1:256 | + | + | + | + |
| Positive control | + | + | + | + |
| MIC | Undilute | Undilute | Undilute | Undilute |

(+) = Growth  (−) = Growth

TABLE 5

| Organism | P.M. | P.A. | S.M. | S.A. | S.B. |
|---|---|---|---|---|---|
| Undilute | − | − | − | − | − |
| 1:2 | + | − | + | − | − |
| 1:4 | + | + | + | + | + |
| 1:8 | + | + | + | + | + |
| 1:16 | + | + | + | + | + |
| 1:32 | + | + | + | + | + |
| 1:64 | + | + | + | + | + |
| 1:128 | + | + | + | + | + |
| 1:256 | + | + | + | + | + |
| Positive control | + | + | + | + | + |
| MIC | Undilute | 1:2 | Undilute | 1:2 | 1:2 |

(+) = Growth  (−) = Growth

The results show that the lotion is effective against all the bacteria used in the study even when diluted to 1:256.

Experiment No. 6

This experiment was performed to determine whether lotion of the present invention is orally toxic. Again, lotion of the formula set forth in example 3 above was used in the experiment.

Healthy, young adult Wistar derived albino rats weighing about 150 to 300 grams were obtained from ACE Animals, Inc., Boyertown, Pa. Five male and five female rats were selected for the dose level chosen for this study.

The rats were fed Purina Rat Chow. Feed and water were supplied ad-libitum. Animals were fasted 18–24 hours prior to dosing. Feed and water were returned ad-libitum immediately thereafter.

Prior to the test period the animals were each uniquely identified with sequentially numbered ear tags and individually housed in wire bottom cages in a temperature controlled room with a 12 hour light/dark cycle. Feed and water were provided ad-libitum after dosing.

During the fast period water was allowed ad-libitum. After fasting rats were individually weighed. All body weights were recorded and individual doses calculated based on these weights. The test material was then delivered by gavage at a dose level of 5.0 g/kg body weight. Once the material had been ingested completely, feed and water were provided ad-libitum. The rats were individually caged and observed for mortality or other signs of gross toxicity for 14 days. At the end of the test period, all surviving animals were weighed. Results of the experiment are reported below in Table 6.

TABLE 6

| Animal # | Sex | Body Weight Initial | Body Weight Final | Dosage (g) | Dose Delivered* (ml) | Mortality Day | Mortality Autopsy |
|---|---|---|---|---|---|---|---|
| 2967 | M | 230 | 289 | 1.15 | 1.16 | NA | NA |
| 2968 | M | 241 | 299 | 1.21 | 1.22 | NA | NA |
| 2969 | M | 175 | 239 | 0.88 | 0.89 | NA | NA |
| 2970 | M | 276 | 300 | 1.38 | 1.39 | NA | NA |
| 2971 | M | 250 | 276 | 1.25 | 1.26 | NA | NA |
| $\bar{x}$ | | 234 | 281 | 1.17 | 1.18 | | |
| 2854 | F | 293 | 293 | 1.47 | 1.48 | NA | NA |
| 2855 | F | 250 | 244 | 1.25 | 1.26 | NA | NA |
| 2856 | F | 259 | 272 | 1.30 | 1.31 | NA | NA |
| 2859 | F | 293 | 293 | 1.47 | 1.48 | NA | NA |
| $\bar{x}$ | | 270 | 272 | 1.36 | 1.37 | | |

*1 ml weights 0.9971 g
NA Not applicable

The results show that the lotion of the present invention is orally non-toxic.

We claim:

1. An antibacterial lotion comprising:
   a polymer mixture comprising polyvinylpyrrolidone and hydroxyethylcellulose in an aqueous solution, wherein the polyvinylpvrrolidone has a molecular weight in the range of 20,000–40,000 daltons and is provided in the solution at a concentration of between approximately 0.10 to 2.00 percent (w/w), and wherein the hydroxyethylcellulose is provided in the solution at a concentration of between approximately 0.10 to 2.00 percent (w/w),
   an antibacterial agent comprising 2,4,4'-trichloro-2'-hydroxydiphenylether or chlorhexidine gluconate, and
   an emulsifying system comprising an emulsifier and an emulsion stabilizer.

2. The lotion of claim 1 further comprising a plasticizer comprising a myristic acid ester.

3. The composition of claim 1, wherein the antibacterial agent is 2,4,4'-trichloro-2'-hydroxydiphenylether ("triclosan").

4. The composition of claim 3, wherein the triclosan is provided in an aqueous solution at a concentration of between about 0.10 to 2.00 percent (w/w).

5. The composition of claim 1, wherein the antibacterial agent is chlorhexidine gluconate.

6. The composition of claim 5, wherein the chlorhexidine gluconate is provided in the aqueous solution at a concentration of between about 0.10 to 3.00 percent (w/w).

7. The composition of claim 1, wherein the emulsification system comprises Lipomulse 165 at a concentration of between approximately 0.50 to 5.00 percent (w/w).

8. The composition of claim 1 further comprising an emulsion stabilizer.

9. The composition of claim 8, wherein the emulsion stabilizer is Crodacol C-95 at a concentration of approximately 0.10 to 2.00 percent (w/w).

10. The lotion of claim 8, wherein the emulsion stabilizer comprises cetyl alcohol.

11. A lotion for topical application on skin comprising:

a polymer mixture comprising polyvinylpyrrolidone and hydroxyethylcellulose in an aqueous solution which dries on skin to form a penetrant barrier for up to several hours after application, wherein the polyvinylpyrrolidone has a molecular weight in the range of 20,000–40,000 daltons and is provided in the solution at a concentration of between approximately 0.10 to 2.00 percent (w/w), and wherein the hvdroxyethylcellulose is provided in the solution at a concentration of between approximately 0.10 to 2.00 percent (w/w), an antibacterial agent dispersed in the solution which is effective for at least about four hours after application on skin to kill a broad spectrum of bacteria which come into contact with the agent, and an emulsifying system comprising an emulsifier and an emulsion stabilizer.

12. The lotion of claim 11, wherein the antibacterial agent is either triclosan or chlorhexidine gluconate.

13. The lotion of claim 11 further comprising an antiviral agent.

14. The lotion of claim 13, wherein the antiviral agent comprises nonylphenol thoxylate.

15. The lotion of claim 11, wherein the polymer mixture comprises an acrylic polymer.

16. The lotion of claim 11, wherein the emulsifying system comprises a mixure of glycerol stearate and polyethylene glycol as an emulsifier, and cetyl alcohol as an emulsion stabilizer.

* * * * *